United States Patent [19]

Tanagho et al.

[11] Patent Number: 4,940,065
[45] Date of Patent: Jul. 10, 1990

[54] SURGICALLY IMPLANTABLE PERIPHERAL NERVE ELECTRODE

[75] Inventors: Emil A. Tanagho; Richard A. Schmidt, San Rafael; Curtis A. Gleason, Palo Alto; Tom F. Lue, Millbrae, all of Calif.

[73] Assignee: Regents of the Univ. of Calif., Berkeley, Calif.

[21] Appl. No.: 299,135

[22] Filed: Jan. 23, 1989

[51] Int. Cl.⁵ ............................................. A61N 1/05
[52] U.S. Cl. ................................................. 128/784
[58] Field of Search ............ 128/784, 785, 642, 419 C

[56] References Cited

U.S. PATENT DOCUMENTS

| | | | |
|---|---|---|---|
| 3,421,511 | 1/1969 | Schwartz et al. | 128/419 C |
| 3,774,618 | 11/1973 | Avery | 128/784 |
| 4,026,300 | 5/1977 | DeLuca et al. | 128/785 |
| 4,602,624 | 7/1986 | Naples et al. | 128/784 |
| 4,750,499 | 6/1988 | Hoffer | 128/784 |

Primary Examiner—Lee S. Cohen

[57] ABSTRACT

An electrode is adapted to be surgically implanted around a nerve bundle to provide for the selective stimulation thereof. The electrode comprises a biocompatible and dielectric carrier formable from a flattened, opened position to a closed position around the nerve bundle. In its opened position, the carrier exhibits a main body portion extending in the direction of a longitudinal wrapping axis of the carrier and flap portions extending transversely outwardly from opposite ends of the main body portion and from the axis. At least one electrode contact is secured on an inner surface of the carrier and is welded to a wire lead, adapted for connection to a receiver implanted on a patient. In carrying forth the method steps for making the electrode, the carrier originally constitutes a tube that is suitably cut to form the main body and flap portions thereof. The electrode contact is then secured to an inner surface of the carrier and welded to the wire lead.

15 Claims, 3 Drawing Sheets

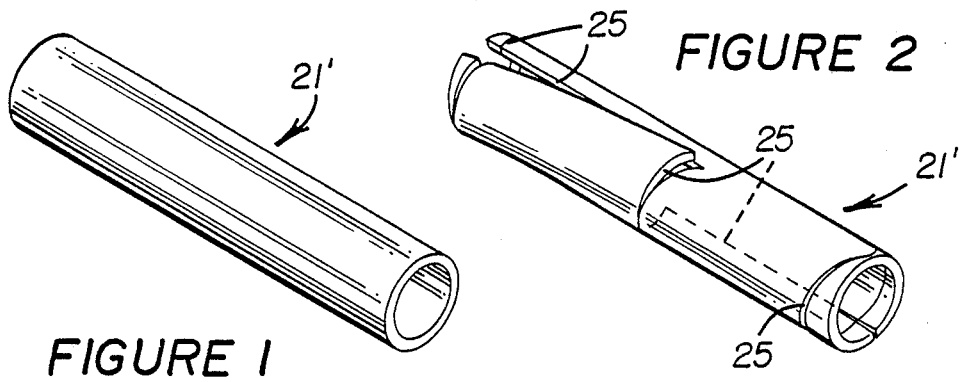
FIGURE 1
FIGURE 2
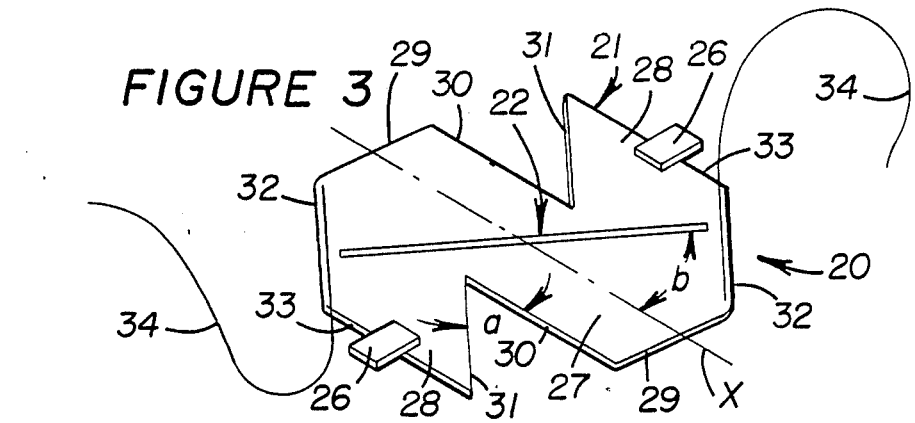
FIGURE 3
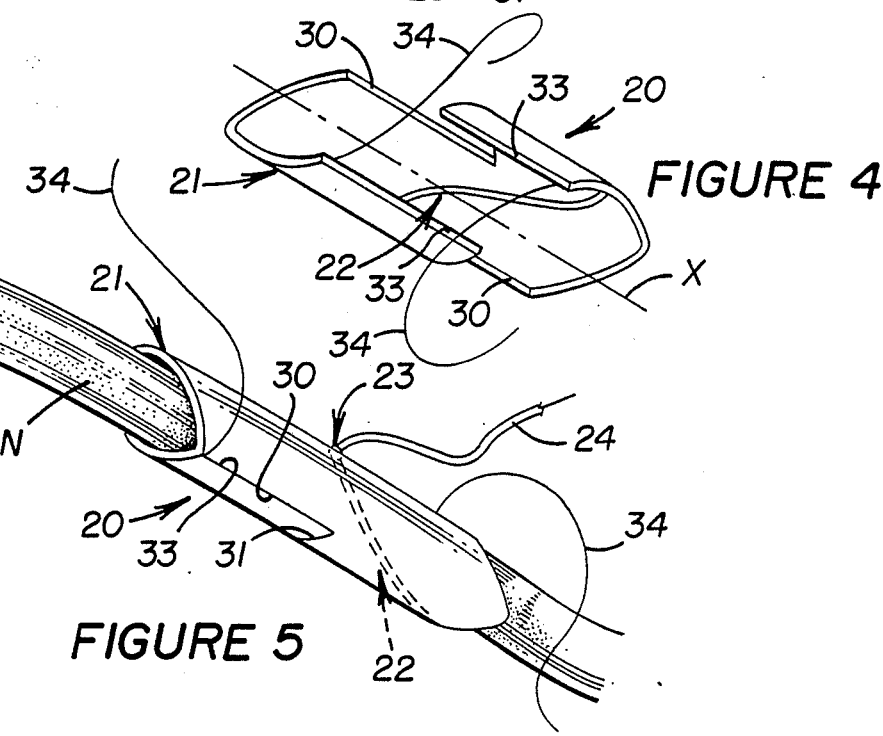
FIGURE 4
FIGURE 5

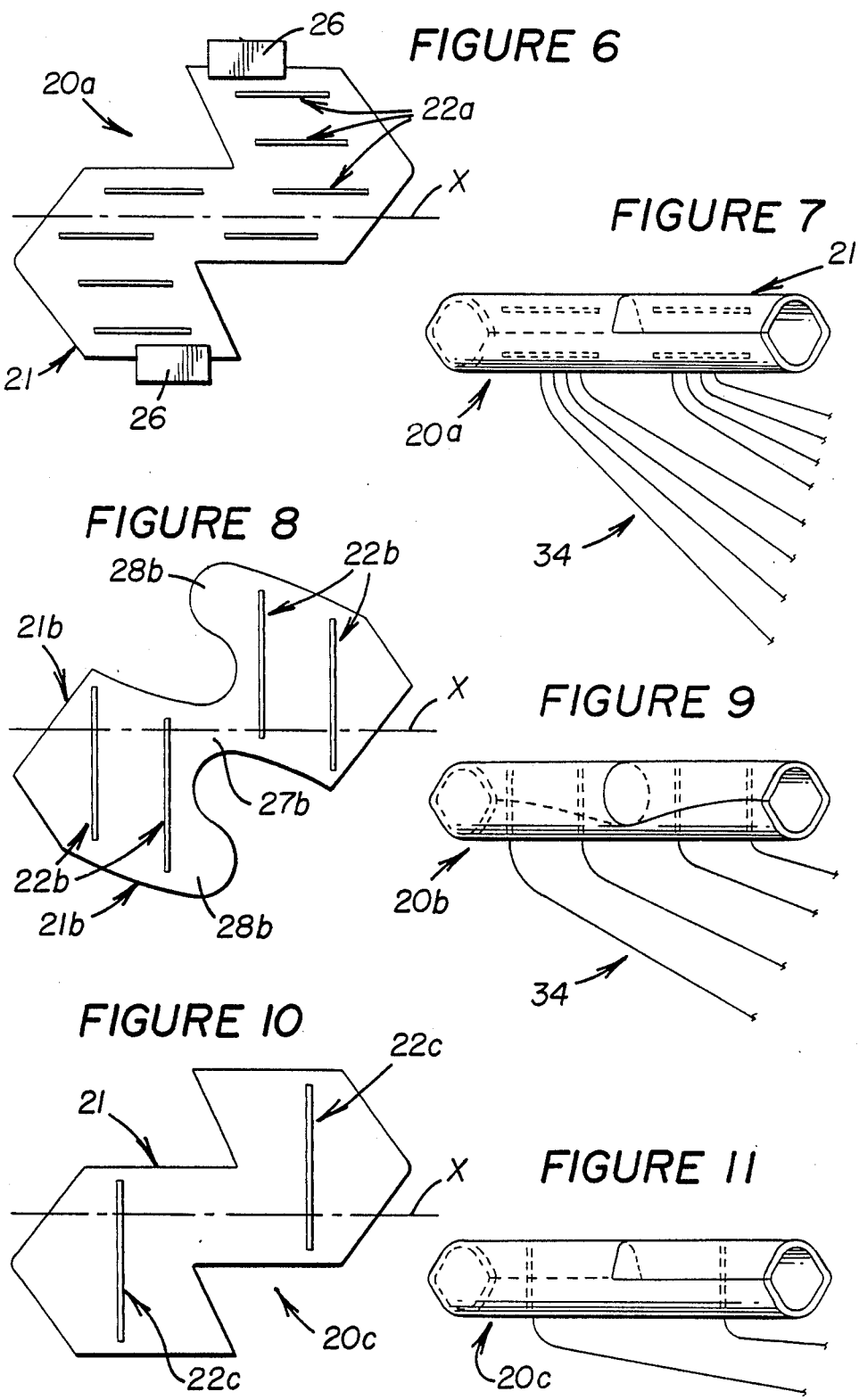

SURGICALLY IMPLANTABLE PERIPHERAL NERVE ELECTRODE

ACKNOWLEDGEMENT

This invention was made with Government support under Grant Contract No. NS-18029 awarded by the DHHS. The Government has certain rights in this invention.

TECHNICAL FIELD

This invention relates generally to an electrode and method for making the same and more particularly to a peripheral nerve electrode adapted to be surgically implanted around a nerve bundle.

BACKGROUND OF THE INVENTION

Electrical stimulation of a peripheral nerve (nerve bundle) is required by certain electro-neuroprostheses to replace or augment physiological body functions that have been compromised or rendered ineffective by disease or trauma. For example, U.S. Pat. Nos. 4,585,005; 4,607,639; and 4,739,764, issued to inventors named herein, disclose systems and methods designed for this purpose. Peripheral nerve electrodes basically consist of a metallic conducting material in the form of an electrode contact having an attached lead and an insulating material that supports the electrode contact.

The electrode contact is connected by its lead to a receiver, implanted on a patient, whereby selective stimulation of the nerve can be achieved in a conventional matter. The insulating material provides a substrate or carrier that functions to hold the electrode contact in a fixed position and further functions as a dielectric to confine electrical current so that it does not affect adjacent nerves, outside of the target area. The electrode contact is normally composed of a platinum-irridium alloy that is innocuous to living tissue, but yet delivers electrical current to the contact at an acceptable level to activate (stimulate) the target nerve. The insulating material composing the carrier is biocompatible, such as a Silastic wrapping or sheeting capable of providing the supporting and dielectric desiderata discussed above.

Various geometric forms of electrode contacts have been proposed, such as small circular or rectangular "buttons" and narrow foil or small wire configurations that are stripped of insulation adjacent to the point whereat a target nerve is positioned. The carrier is normally formed as a "cuff" that encircles the nerve or as a "spiral" that wraps around the nerve. The so-called cuff electrode is placed around the nerve to form a continuous slit between adjacent edges thereof. Sutures or staples are normally used to attach the two adjacent edges of the cuff electrode together.

Application of these sutures or staples to the cuff electrode requires a delicate surgical procedure after the cuff electrode is placed on the nerve. Unless the separation line between the opposing edges of the cuff electrode is properly sealed, the nerve is susceptible to herniation upon the growth of post-surgical tissue within the electrode lumen.

Another problem encountered with the use of the cuff electrode is the relative rigidity of the carrier to which the electrode contact is secured when the carrier is wrapped around a nerve. In particular, when the carrier is formed into a cylinder around the nerve, no space is left for accommodating tissue expansion when tissue grows between the electrode contact and the carrier whereby the nerve will assume a confined, constricted volume. Thus, in order to prevent such constriction, the cuff electrode must be formed to have a relatively larger diameter than the nerve to which it is attached to allow for such tissue growth. The use of an oversized cuff electrode obviously decreases the efficiency of the stimulus/electrode system.

In the case of the spiral electrode, the composite outer diameter thereof will normally increase to accommodate tissue growth. However, since the spirals of the electrode that wrap around the nerve are relatively narrow, the desired insulating properties of the spiral electrode will be absent. Therefore, non-targeted nerves, adjacent to the target nerve, will be stimulated by the leakage of current, particularly when relatively high current levels are used.

SUMMARY OF THE INVENTION

An object to this invention is to provide an improved peripheral nerve electrode adapted for surgical implantation around a nerve and a method for making such electrode.

The electrode comprises a carrier formable about a longitudinal wrapping axis thereof from an opened position to a closed position, encircling a nerve. The carrier is composed of a biocompatible and dielectric material and, when in its opened position, the carrier exhibits a main body portion extending in a direction of such axis and flap portions extending transversely outwardly from opposite ends of the main body portion and from the axis. One or more electrode contacts are secured on an inner surface of the carrier for selectively electrically stimulating the nerve when the carrier is in its closed position thereabout.

In carrying forth the method steps of this invention, the electrode is formed by first cutting a tube into the shape of the carrier and then securing one or more electrode contacts thereto.

BRIEF DESCRIPTION OF THE DRAWINGS

Other objects and advantages of this invention will become apparent from the following description of the accompanying drawings wherein:

FIG. 1 is an isometric view of a plastic tube adapted to be formed into a carrier or substrate for a peripheral nerve electrode of this invention;

FIG. 2 is an isometric view illustrating the tube in its cut condition to form the carrier;

FIG. 3 is an isometric view illustrating the carrier in its opened and flattened condition with a wire electrode contact and a pair of optional sutures secured thereon to form the peripheral nerve electrode;

FIG. 4 illustrates the carrier and formed electrode in a partially wrapped condition prior to its application to a nerve bundle;

FIG. 5 is a isometric view illustrating application of the carrier and formed electrode to a nerve bundle and the further securance of an electrical lead to the electrode contact thereof;

FIG. 6 is a top plan view of a first modification of the peripheral nerve electrode with the electrode shown in its opened, flattened condition;

FIG. 7 illustrates the FIG. 6 electrode in its closed position as it would appear wrapped around a nerve bundle;

FIGS. 8 and 9 are views similar to FIGS. 6 and 7, respectively, but illustrate a second modification of a peripheral nerve electrode;

FIGS. 10 and 11 are views similar to FIGS. 6 and 7, respectively, but illustrate a third modification of the peripheral nerve electrode;

DESCRIPTION OF THE PREFERRED EMBODIMENT

Figure 12:
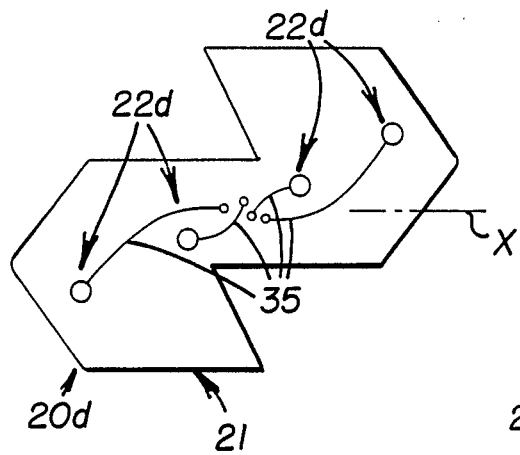
FIGS. 12 and 13 are views similar to FIGS. 6 and 7, respectively, but illustrate a fourth modification of the peripheral nerve electrode.

FIGS. 1-5 sequentially illustrate a method for forming a peripheral nerve electrode 20 and surgically implanting the electrode around a nerve (nerve bundle) N. As shown in FIG. 5, the electrode comprises a substrate or carrier 21 having an electrode contact 22 secured therein for the purpose of selectively stimulating the nerve. The electrode contact is welded at 23 to an electrical lead 24, adapted for connection to a receiver (not shown) implanted on a patient in a manner described in above referenced U.S. Pat. Nos. 4,585,005; 4,607,639; and 4,739,764.

In carrying forth the method steps for making electrode 20, a cylindrical tube 21' shown in FIG. 1 is held in a suitable fixture (not shown) and then formed with cuts 25 and further cuts to remove a truncated portion 30 at each end of the tube. The tube, forming carrier 21, may be composed of any suitable biocompatible and dielectric material commonly used for this purpose. For example, the material may constitute Silastic which is a composition in physical character comparable to milled and compounded rubber prior to vulcanization, but containing organosilicon polymers.

Carriers or substrates fabricated from this material are serviceable from −73° to +160° C., retain good physical and dielectric properties when placed in a patient, exhibit excellent resistance to compression set, weathering, and corona. In addition, thermal conductivity of this material is high and water absorption is low. When cut in tube form, as illustrated in FIG. 1, the Silastic material will also exhibit physical properties (flexibility, modulus of elasticity, etc.) whereby the tube, when cut and flattened to its FIG. 3 condition will exhibit sufficient "memory" to automatically reassume its cylindrical configuration illustrated in FIG. 5.

Referring to FIG. 3, after the tube has been cut it is flattened and preferably held by two or more clamps 26 for securance of electrode contact 22 thereto. The electrode contact is preferably composed of a standard platinum-irridium alloy that is innocuous to living tissue, but yet delivers electrical current at an acceptable level to stimulate a target nerve. The electrode contact may be preformed into a standard ribbon or wire configuration or may comprise a plurality of interconnected button electrode contacts, described more fully hereinafter with reference to the embodiments illustrated in FIGS. 12-15.

As shown in FIG. 3, flattened carrier 21 is formable above a longitudinal wrapping axis X of the electrode from its illustrated opened position to its closed position illustrated in FIG. 5, encircling nerve N. In its opened position, main body portion 27 is defined by a pair of opposite end edges 29 and parallel side edges 30 intersecting the end edges. Each flap portion 28 is defined by a pair of parallel side edges 31 and 32 each defining an acute angle "a" relative to a respective edge 30, shown as an approximating 60°.

Each outer side edge 32 and intersecting edge 29 are defined when a respective truncated end portion of tube 21' is cut-off the tube. Parallel distal edge 33 of flap portion 28 are preferably disposed in parallel relationship relative to wrapping axis X of the carrier.

When the carrier is thus viewed in plan, (flattened) it assumes a general Z-shape to facilitate its compact wrapping about nerve N, as illustrated in FIG. 5. When the carrier is so wrapped, each edge 30 of main body portion 27 will closely abut distal edge 33 of a respective flap portion 28 whereas inner edges 31 will also be placed in close abutting relationship relative to each other. Thus, the carrier will again assume its substantial cylindrical configuration illustrated in FIGS. 2 and 5 (with the truncated ends of the cylinder removed). As discussed above, the plastic material composing the carrier will preferably exhibit a "memory" whereby it will automatically reassume its cylindrical configuration when placed about the nerve.

Referring to FIG. 3, electrode contact 22 is shown in a form of a ribbon or wire extending transversely across main body portion 27 of the carrier, between outer side edges 32 of the flap portions thereof. As shown, the electrode contact further extends transversely across wrapping axis X of the carrier and is disposed at an acute angle "b", shown as approximating 35°.

Electrode contact 22 may be secured to the inner surface of carrier 21 by a suitable adhesive, such as the material composing the carrier, or can remain unattached except for welds 23 (FIG. 5). A Silastic could also be used to more firmly secure weld 23 and lead 24 to outside of the carrier, if so desired. In certain applications, it may prove desirable to secure sutures 34 to carrier 21 to aid in retaining the carrier and integrated electrode on nerve N. One of the desired results in applying the herein described electrodes to a nerve is that the electrical stimulation be applied at least substantially circumferentially (360°) about all of the quadrants of the nerve.

FIGS. 6 and 7 illustrate a modification 20a of peripheral nerve electrode 20 wherein identical numerals depict corresponding components with numerals depicting modified components being accompanying by an "a." A similar numbering system is used to describe the embodiments illustrated in FIGS. 8-15.

FIGS. 6 and 7 illustrate a four-pair inline electrode configuration wherein a plurality of wire or ribbon electrode contacts 22a are secured in place on an inner surface of carrier 21 and are welded externally of the carrier to leads 34 in the manner described above. In the illustrated embodiment, electrode contacts 22a are disposed in parallel relationship relative to each together and to the longitudinal wrapping axis of the carrier.

FIGS. 8 and 9 illustrate a quadripolar electrode configuration 20b wherein a plurality of wire or ribbon electrode contacts 22b are disposed in parallel relationship relative to each other and perpendicularly or transversely relative to wrapping axis X of carrier 21b. The modified carrier exhibits a general hour glass shape wherein a main body portion 27b is in the form of a web interconnecting transversely extending flap portions 28b. Leads 34 are welded to the electrode contacts in the manner described above.

FIGS. 10 and 11 illustrate a bipolar electrode configuration 20c wherein a pair of longitudinally spaced electrode contacts 22c are disposed in parallel relationship to each other and in perpendicularly or transverse relationship relative to wrapping axis X of carrier 21. Leads 34 are welded to the electrode contacts in the manner described above.

Figure 13:
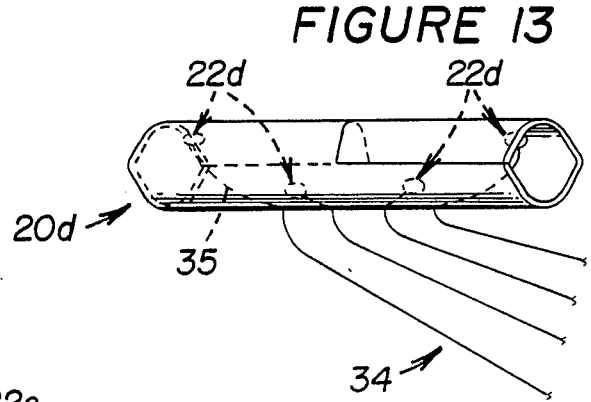

FIGS. 12 and 13 illustrate a four-lead monopolar separated electrode configuration 20d wherein a plurality of button-type (circular or multi-sided) electrode contacts 22d are secured on the inner surface of carrier 21. Additional leads 35 are disposed on the inner surface of carrier 21 and interconnect the electrode contacts with outer leads 34. It should be noted in FIG. 12 that when electrode contacts 22d are secured to the inner surface of carrier 21 that they are disposed in linear relationship relative to each other and are further disposed transversely across the main body portion of the carrier, i.e., similar to FIG. 3. When formed into a general cylindrical shape, as illustrated in FIG. 13, the electrode contacts will thus be spaced circumferentially approximately 90° from each adjacent electrode contact whereby four quadrants of a nerve bundle will be stimulated.

Figure 14:
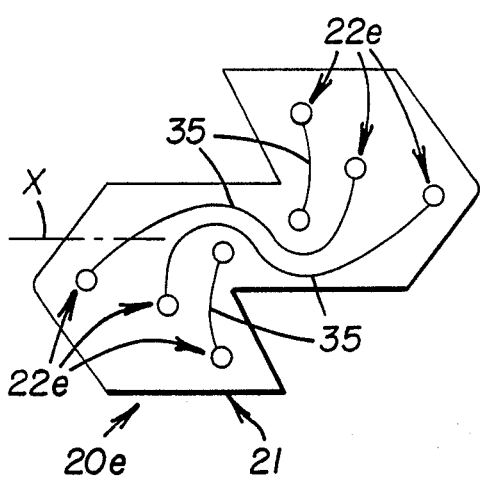
FIGS. 14 and 15 are views similar to FIGS. 6 and 7, but illustrate a fifth modification of the peripheral nerve electrode.
Figure 15:
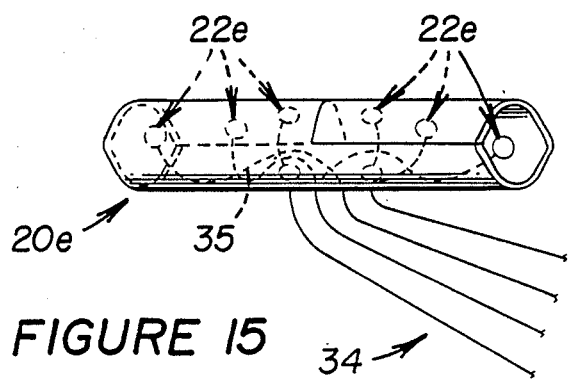

FIGS. 14 and 15 illustrate a four-lead bipolar and paired electrode configuration 20e comprising eight electrode contacts 22e. As shown, internal leads 35 interconnect each mating pair of electrode contacts together which are then connected to external leads 34.

I claim:

1. A peripheral nerve electrode adapted to be surgically implanted around a nerve comprising
    carrier means formable about a longitudinal wrapping axis thereof from an opened position to a closed position encircling a nerve, said carrier means composed of a biocompatible and dielectric material and when in its opened position said carrier means having a main body portion extending in the direction of said axis and flap portions extending transversely outwardly from opposite ends of said main body portion and from said axis and when in its closed position said carrier means having opposed edges of opposite sides of its main body and flap portions disposed in close abutting relationship relative to each other to form a tube, and
    electrode means secured on an inner surface of said carrier means for selectively electrically stimulating said nerve when said carrier means is in its closed position thereabout.

2. The nerve electrode of claim 1 wherein said carrier means generally forms a cylindrical tube when in its closed position and is composed of a polymeric material exhibiting a memory to automatically assume its closed position when released from its opened position.

3. The nerve electrode of claim 2 wherein said carrier means is composed of a polymeric material having a physical character comparable to milled and compounded rubber prior to vulcanization, but containing organosilicon polymers.

4. The nerve electrode of claim 1 wherein said carrier means is generally Z-shaped when in its opened and flattened position and said main body portion is defined by a pair of opposite end edges disposed transversely relative to said axis and parallel side edges intersecting said end edges.

5. The nerve electrode of claim 4 wherein each said flap portion is defined by a pair of parallel outer and inner side edges each defining an acute angle relative to said axis and to a respective one of the side edges of said main body portion.

6. The nerve electrode of claim 5 wherein said outer and inner side edges intersect a respective one of the end edges and side edges of said main body portion, respectively.

7. The nerve electrode of claim 6 wherein each said flap portion is further defined by a distal edge intersecting the outer and inner edges thereof and when said carrier means is in its closed position each side edge of said main body portion being disposed to closely abut a distal edge of a respective flap portion and the inner edges of said flap portions being disposed to closely abut each other with said carrier means generally assuming a cylindrical configuration.

8. The nerve electrode of claim 1 wherein said electrode means extends at least substantially circumferentially within said carrier means and about said nerve when said nerve electrode is in its closed position encircling said nerve.

9. The nerve electrode of claim 8 wherein said electrode means comprises a wire or ribbon electrode contact extending transversely across said main body portion, between outer side edges of said flap portions.

10. The nerve electrode of claim 8 wherein said electrode means comprises a plurality of wire or ribbon electrode contacts disposed in spaced and parallel relationship relative to each other.

11. The nerve electrode of claim 10 wherein said electrode contacts are disposed in parallel relationship relative to said axis.

12. The nerve electrode of claim 10 wherein said electrode contacts are disposed transversely relative to said axis.

13. The nerve electrode of claim 8 wherein said electrode means comprises a plurality of button-type electrode contacts.

14. The nerve electrode of claim 1 further comprising an electrical lead means welded to said electrode means for connecting said electrode means to a receiver implanted on a patient.

15. A peripheral nerve electrode adapted to be surgically implanted around a nerve comprising
    carrier means formable about a longitudinal wrapping axis thereof from an opened position to a closed position encircling a nerve, said carrier means composed of a biocompatible and dielectric material and when in its opened position said carrier means having a main body portion extending in the direction of said axis and flap portions extending transversely outwardly from opposite ends of said main body portion and from said axis, said carrier means being generally Z-shaped when in its opened and flattened position and said main body portion being defined by a pair of opposite end edges disposed transversely relative to said axis and parallel side edges intersecting said end edges, and
    electrode means secured on an inner surface of said carrier means for selectively electrically stimulating said nerve when said carrier means is in its closed position thereabout.

* * * * *